United States Patent [19]

Borror et al.

[11] 4,250,244

[45] Feb. 10, 1981

[54] THIACYANINE BETAINE BLUE SENSITIZING DYES

[75] Inventors: Alan L. Borror, Lexington; Ruth L. Hill, Cambridge, both of Mass.

[73] Assignee: Polaroid Corporation, Cambridge, Mass.

[21] Appl. No.: 764,730

[22] Filed: Feb. 2, 1977

[51] Int. Cl.$^3$ .................. G03C 1/40; G03C 1/16; G03C 1/18; G03C 1/20
[52] U.S. Cl. ..................... 430/217; 430/505; 430/560; 430/583; 542/452
[58] Field of Search ............ 96/3, 29 D, 77, 73, 96/132, 99, 76 C; 260/240 F, 240.7; 430/217, 583, 505, 560

[56] References Cited

U.S. PATENT DOCUMENTS

| 2,503,776 | 4/1970 | Sprague | 96/132 |
|---|---|---|---|
| 3,177,210 | 4/1965 | Rosenoff et al. | 96/137 |
| 3,415,646 | 12/1968 | Land | 96/77 |
| 3,752,670 | 8/1973 | Needler et al. | 96/132 |
| 3,847,613 | 11/1974 | Sakazume et al. | 96/132 |
| 3,930,862 | 1/1976 | Tsubota et al. | 96/77 |
| 3,982,946 | 9/1976 | Maekawa et al. | 96/77 |
| 3,986,878 | 10/1976 | Hinata et al. | 96/132 |

Primary Examiner—Richard L. Schilling
Attorney, Agent, or Firm—Philip G. Kiely

[57] ABSTRACT

Photosensitivity of a blue-sensitive emulsion in a multicolor diffusion transfer photographic system is enhanced by sensitizing the emulsion with certain 3,3'-disubstituted 4,5-benzothia-thiacyanine betaines.

15 Claims, No Drawings

THIACYANINE BETAINE BLUE SENSITIZING DYES

BACKGROUND OF THE INVENTION

In the photographic art, a photosensitive element comprising a support carrying a red-sensitive silver halide emulsion having associated therewith a cyan dye developer, a green-sensitive silver halide emulsion having associated therewith a magenta dye developer and a blue-sensitive silver halide emulsion having associated therewith a yellow dye developer is known. Photographic film units are also known in which such photosensitive elements have a diffusion transfer image-receiving element affixed to at least one edge thereof, the diffusion transfer image-receiving element being a support layer which carries an alkaline processing composition permeable and dyeable layer, the image-receiving element and photosensitive element being adapted to be superposed with the support layers being the extremities of the superposed structure.

The basic photosensitive element is taught in U.S. Pat. No. 2,983,606. The element contains a dye developer, i.e., a dye which is a silver halide developing agent, and a silver halide emulsion, and can be exposed to actinic radiation and wetted by a liquid processing composition by immersion, coating, spraying, flowing, etc., in the dark, and the exposed photosensitive element is superposed prior to, during, or after wetting, or a sheet-like support element which may be utilized as an image-receiving element. The liquid processing composition can be applied to the photosensitive element in a substantially uniform layer as the photosensitive element is brought into superposed relationship with the image-receiving layer and, positioned intermediate the photosensitive element and the image-receiving layer, permeates the emulsion to initiate development of the latent image contained therein. The dye developer is immobilized or precipitated in exposed areas as a consequence of the development of the latent image. In unexposed and partially exposed areas of the emulsion, the dye developer is unreacted and diffusible and thus provides an imagewise distribution of unoxidized dye developer dissolved in the liquid processing composition, as a function of the point-to-point degree of exposure of the silver halide emulsion. At least part of this imagewise distribution of unoxidized dye developer is transferred, by diffusion, to a superposed image-receiving layer or element, said transfer substantially excluding oxidized dye developer. The image-receiving element receives a depthwise diffusion from the developed emulsion of unoxidized dye developer without appreciably disturbing the imagewise distribution thereof to provide the reversed or positive color image of the developed image. The image-receiving element can contain agents adapted to mordant or otherwise fix the diffused, unoxidized dye developer. In one embodiment, the desired positive image is revealed by stripping the image-receiving layer from the photosensitive element at the end of a suitable imbibition period.

The dye developers are compounds which contain both the chromophoric system of a dye and also a silver halide developing function of the same molecule. By "a silver halide developing function" is meant a grouping adapted to develop exposed silver halide. A preferred silver halide development function is a hydroquinonyl group. Other suitable developing functions include ortho-dihydroxyphenyl and ortho- and para-amino substituted hydroxyphenyl groups. In general, the development function includes a benzenoid developing function, i.e., an aromatic developing group which forms quinonoid or quinone substances when oxidized.

Multicolor images may be obtained using color image-forming components such as, e.g., the previously mentioned dye developers, in diffusion transfer processes by several techniques. One such technique involves utilizing dye developers by employment of an integral multilayer photosensitive element, as disclosed in U.S. Pat. No. 2,983,606, wherein at least two selectively sensitized photosensitive strata superposed on a single support are processed simultaneously and without separation, with a single, common image-receiving layer. A suitable arrangement of this type comprises a support carrying a red-sensitive silver halide emulsion stratum, a green-sensitive silver halide emulsion stratum and a blue-sensitive silver halide emulsion stratum, the emulsions having associated therewith, respectively, e.g., a cyan dye developer, a magenta dye developer and a yellow dye developer. The dye developer may be utilized in the silver halide emulsion layer, e.g., in the form of particles, or it may be employed as a layer behind the appropriate silver halide emulsion strata. Each set of silver halide emulsion and associated dye developer strata are optionally separated from other sets by suitable interlayers, e.g., by a layer of gelatin or polyvinyl alcohol. In certain instances, it may be desirable to incorporate a yellow filter in front of the green-sensitive emulsion and such yellow dye developer of the appropriate spectral characteristics and capable of functioning as a yellow filter may be employed, and in such instances, a separate yellow filter may be omitted.

The dye developers are dye-image forming materials which are preferably selected for their ability to provide colors that are useful in carrying out subtractive color photography, i.e., the previously mentioned cyan, magenta and yellow. The dye developers employed may be incorporated in the respective silver halide emulsion or, in a preferred embodiment, in a separate layer behind the respective silver halide emulsion. Specifically, the dye developer may, e.g., be in a coating or layer behind the respective silver halide emulsion and such a layer of dye developer may be applied by use of a coating solution containing about 0.5 to 8% by weight of the respective dye developer distributed in a film-forming natural, or synthetic, polymer, such as gelatin, polyvinyl alcohol, and the like, adapted to be permeated by the chosen diffusion transfer fluid processing composition.

An extensive compilation of specific dye developers particularly adapted for employment in photographic diffusion transfer processes is set forth in aforementioned U.S. Pat. No. 2,983,606 and in the various co-pending U.S. applications referred to in that patent and also in U.S. Pat. Nos. 2,983,605; 2,992,106; 3,047,386; 3,076,808; 3,076,820; 3,077,402; 3,126,280; 3,131,061; 3,134,762; 3,134,765; 3,135,604; 3,135,605; 3,135,606; 3,135,734; 3,141,772; 3,142,565; 3,563,739; 3,551,406; 3,597,200, 3,482,972 and 3,705,184.

It should be understood that the dye developers may contain the specified color initially or the spectral absorption may be temporarily shifted, particularly if the dye developer is disposed in the emulsion layer. The term "dye developer" as used herein is intended to include color shifted dye developers as well as those possessing initially the desired absorption over a given spectral range.

It is preferred that the dye developer be retained in gelatin, however, other natural and synthetic materials may also be employed.

U.S. Pat. No. 3,362,819 teaches image-receiving elements particularly adapted for employment in the preceding diffusion transfer processes which comprise a support layer possessing on one surface thereof, in sequence, a polymeric acid layer, preferably an inert timing or spacer layer, and an image-receiving layer adapted to provide a visible image upon transfer to said layer of diffusible dye image-forming substance.

Silver halide emulsions having a relatively high iodine content, i.e., at least 3 mole percent iodine, generally provide good results when used as the blue-sensitive halide emulsion in the photosensitive elements and film units described above. However, silver halide emulsions which have relatively low iodine content, i.e., less than about 2 mole percent, and which have not been spectrally sensitized, have limited response to longer blue wave length radiation. It is therefore usually necessary to spectrally sensitize such emulsions in order to adjust the sensitivity distribution of the emulsion. Spectral sensitizers can also be used to increase the speed of the emulsion. Without such sensitizers, the response of the emulsion to radiation having a wave length between about 460 and 500 nm is less than desired.

For some time, those skilled in the art have been aware of thiacyanine sensitizers which are generic to the blue sensitizers used in the present invention. In this connection, note should be taken of British Pat. No. 1,252,066 and U.S. Pat. No. 3,177,210. The use of similar sensitizers in a color coupling system is taught by U.S. Pat. No. 3,847,613.

Prior to the present invention, some of the preferred thiacyanine sensitizers were those of copending application Ser. No. 297,456 filed Oct. 13, 1972 now abandoned and replaced by continuation application Ser. No. 766,225, filed Feb. 7, 1977 and represented by the formula:

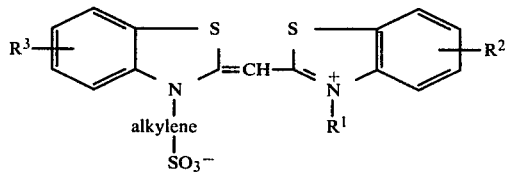

(A)

wherein $R^1$ is a lower alkyl group, i.e., 1–4 carbon atoms; $R^2$ and $R^3$ are alkyl, alkoxy, halogen or hydrogen, and the alkylene group contains between 1 and 18 carbon atoms inclusive.

Within this group, a particularly interesting material is:

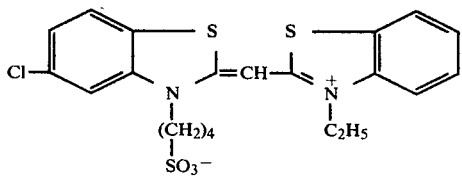

(I)

anhydro 5-chloro-3'-ethyl-3-(4-sulfobutyl)-thiacyanine hydroxide (hereinafter referred to as "compound I").

As shown below, in Table 1 compound I can extend the blue sensitivity to 478 nm with a maximum at 465 nm. The sensitivity at the maximum is equivalent to the intrinsic as measured on the wedge spectrogram. Moreover, this sensitizer imparts a good speed to the emulsion.

While compound I is a superior blue sensitizer, it is not without its deficiencies. The response of compound I sensitized low iodide emulsions to radiation of 479 to 500 nm is limited. Also, in order to obtain good color reproduction, the blue speed of the color film must be balanced against the green speed. Some yellow dye developers require a faster blue emulsion to properly control dye transfer.

By employing some of the thiacyanines of formula A other than compound I (i.e., by varying the $R^1$, $R^2$, $R^3$ and alkylene moieties), it has been found possible to increase the extent of sensitivity. It has not been found possible, however, to achieve any greater speed with such other thiacyanine dyes of formula A than is achieved with compound I. Moreover, the use of such other thiacyanine dyes is often accompanied by a loss in the maximum density of the dye transfer wedge obtained from the emulsion (hereinafter D-max) and such a decrease in D-max can be due to fog in the emulsion.

As is apparent from the foregoing, there is still a need for an improved blue sensitizer which can extend the blue sensitivity to as close to 500 nm as possible without a loss in D-max while simultaneously imparting an increased speed to the emulsion and yet facilitating attaining the desired balance between the speed of the green and blue emulsions, and which also exhibits an increased immunity to sensitivity loss in the presence of emulsion stabilizers. Since the green region begins at 501 nm, it is also apparent that such sensitizers must also be characterized by exhibiting a sharp cut off of sensitizer effectiveness at 490 to 500 nm. Such a delicate balance of properties is obviously difficult to achieve.

It is the object of this invention to provide such improved blue sensitizers, photosensitive elements and photographic film units containing such sensitizers. This and other objects of the inventions will become apparent from the following detailed description of the invention.

SUMMARY OF THE INVENTION

The present invention relates to certain thiacyanine betaines and their utilization for the enhancement of the blue response in a typical diffusion transfer photosensitive element as described above. More particularly, it has been discovered that the sensitivity of the blue portion of the visible spectrum of a silver halide photosensitive emulsion utilized in conjunction with a dye developer in a diffusion transfer photographic environment can be enhanced by incorporating into such emulsion a sensitizing dye of the formula:

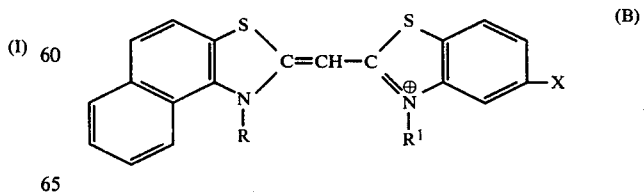

(B)

in which R is methyl, ethyl, or sulfopropyl, $R^1$ is alkyl of 1 to 4 carbon atoms or sulfoalkylene of between 1 and 4 carbon atoms, only one of R and $R^1$ being a sulfo moiety, and in which X is hydrogen, fluorine, chlorine or methyl. The blue sensitivity of the emulsion is extended beyond the region of the inherent sensitivity without any loss in the inherent region. The sensitivity is extended very close to 500 nm with a sharp cut off of sensitizer effectiveness at 490-500 nm, the balance between the speed of the blue and green emulsions is appropriate, the blue emulsion exhibits increased speed without a loss in D-max, and the dyes of the present invention are more strongly adsorbed to the silver halide grain and not easily displaced by stabilizers. This delicate balance of properties remains within desirable limits over a 7°-35° C. range in processing.

DETAILED DESCRIPTION OF THE INVENTION

The sensitizers used in the present invention are water insoluble 3,3'-disubstituted 4,5-benzothia-thiacyanine betaines corresponding to the formula:

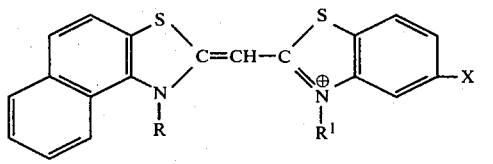

(B)

wherein R is methyl, ethyl or sulfopropyl, $R^1$ is alkyl of 1 to 4 carbon atoms or sulfoalkylene of between 1 and 4 carbon atoms, only one of R and $R^1$ being a sulfo moiety, and X is hydrogen, fluorine, chlorine or methyl. The sensitizers can be prepared by conventional techniques as taught, for example, in U.S. Pat. Nos. 2,504,776; 3,177,210 and 3,847,613 and British Pat. No. 1,252,066.

The sensitizers are incorporated into the emulsion by well-known techniques, such as by being uniformly distributed throughout a washed, finished emulsion in a concentration dependent on the sensitometric characteristics of the particular emulsion and the effect desired. Generally, between 0.05 to 4.0 mgs of dye per gram of silver, preferably about 1 mg of dye per gram of silver, is employed. The sensitizers are preferably added to the emulsion in a suitable solvent such as methanol, ethanol, trifluroethanol, etc. slowly and under constant stirring. The sensitized emulsion can then be handled, stored and coated according to conventional techniques.

A requisite function of the dye sensitizers of the present invention is that they be non-migratory—for were they to diffuse, they might provide a chromatically deleterious effect to any ultimate image formed. In general, the migration propensities of the denoted sensitizers may best be controlled by choosing appropriate alkylene groups in the generic formula above. However, it must be observed that as shown infra, compounds very close in structure to the instant sensitizers do not provide the very sensitive balance of desirable properties contributed by the instant materials.

It will be appreciated that enhancement of the blue response in the diffusion transfer photosensitive systems described above by the instant dye sensitizers is advantageous because of the thinness of the silver halide emulsion layer, the low iodide (less than about 2 mole percent) content of the blue-sensitive emulsion used as well as the possible utilization of an ultra-violet light-absorbing material which removes much of the electromagnetic radiation which would ordinarily promote latent image formation in blue-sensitive emulsion.

In order to further illustrate the present invention, various examples are given hereinafter. Throughout this specification and claims, all parts and percentages are by weight and all temperatures in degrees centigrade unless otherwise indicated. Further, all sensitometric data was obtained using an exposure of 2 meter-candle seconds for 1/125 of a second and Xenon lamp color corrected to 5500° K. as the source of light. All spectra referred to herein are emulsion spectra.

PREPARATION OF THE SENSITIZERS

Example 1

75 grams of 2-methyl-3-sulfopropyl-β-naphtholthiazolium betaine was suspended in 2600 ml of ethanol and heated to reflux for fifteen minutes in a 5 liter, 3-neck round-bottom flask, equipped with a stirrer, condenser and dropping funnel. 92.5 grams of 3-ethyl-2-ethylthiobenzothiozolium tosylate was added to the reaction mixture. 42.5 ml of triethylamine was added dropwise and the stirred suspension was maintained at reflux for 40 minutes. 900 ml of water was then added all at once, and the heating was continued for an additional ten minutes. The dye suspension was filtered hot through a Buchner funnel, washed with boiling water, hot methanol and hot methyl Cellosolve. Thereafter, the resulting dye was dried in a 65° C. vacuum desiccator overnight resulting in the production of 73.4 grams of a yellow powder. The yield was 65% of 3-(3-sulfopropyl)-3'-ethyl-4,5-benzothia-thiacyanine betaine:

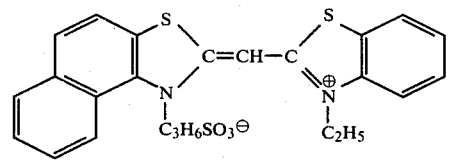

Example 2

2.23 grams of 2-methyl-3-(3'-sulfopropyl) benzothiazolium betaine was dissolved in 10 grams of phenol at 85° C. and 1.36 grams of 2-ethylthio-3-ethyl-β-naphtholthiazolium tosylate was added followed by 0.7 ml of triethylamine. The reaction mixture was maintained at 85° C. for 0.25 hour and then cooled. Acetone was added resulting in the precipitation of a bright yellow solid. The dye was collected, washed well with acetone, boiled in methyl Cellosolve, and then filtered while still hot to obtain an orange solid. The solid was vacuum dried at 65° C. 1.9 grams of product was thus obtained. The yield was 79.2% of 3-ethyl-3'-(3-sulfopropyl)-4,5-benzothia-thiacyanine betaine:

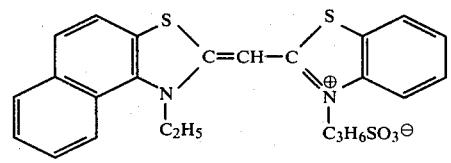

Example 3

2.23 grams of 2,5-dimethyl-3-(3-sulfopropyl) benzothiazolium betaine was dissolved in 10 grams of phenol at 80° C. in a 100 ml, 3-neck flask equipped with a mechanical stirrer and a condenser. 1.43 grams of 2-ethylthio-3-ethyl-β-naphtholthiazolium tosylate was added followed by 0.7 ml of triethylamine. The reaction mixture was heated at 80° C. for 0.25 hour and then allowed to cool slightly and acetone added. The mixture was allowed to sit resulting in the precipitation of a yellow solid. The crude dye was then recrystallized from 1 liter of methyl Cellosolve and 300 ml of trifluorethanol. 2.0 grams of recrystallized dye were recovered representing a yield of 80.6% of 3-ethyl-3'-(3-sulfopropyl)-5'-methyl-4,5-benzothia-thiacyanine betaine:

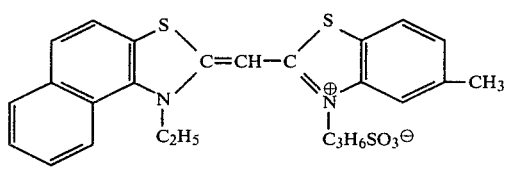

Example 4

2.2 grams of 3-ethyl-2-ethylthio-β-naphtholthiazolium tosylate, 1.45 grams of 2-methyl-5-fluoro-3-sulfopropyl benzothiazolium betaine and 5 grams of phenol were heated to 100° C., 0.7 ml of triethylamine was added and the solution maintained at 100° C. for 0.25 hour. Upon cooling, a suspension was obtained. Acetone was added with stirring, and the resulting solid was collected and washed well with acetone until the reddish color was eliminated. The solid was then heated with methyl Cellosolve and filtered. The solid was then washed with ether and dried in a 65° vacuum desiccator overnight, resulting in 1.3 grams of a yellow fibrous solid, 3-methyl-3'-(3-sulfopropyl)-5'-fluoro-4,5-benzothia-thiacyanine betaine:

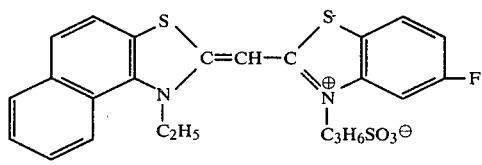

Example 5

3.24 grams of 3-ethyl-2-ethylthio-β-naphtholthiazolium tosylate and 2.23 grams of 2-methyl-5-chloro-3-sulfopropyl-benzothiazolium betaine were combined with 30 ml ethanol in a 100 ml 3-neck flask equipped with a mechanical stirrer and a condenser. Triethylamine (1.02 ml) was added and reaction mixture refluxed for 30 minutes. The reaction mixture was then allowed to cool to room temperature. The dye was collected, washed with acetone, and then boiled in 400 ml of methyl Cellosolve. The mixture was filtered hot and the dye air dried overnight. After vacuum drying at 60° C., 3.0 grams of product was obtained representing a yield of 79.6% of 3-ethyl-3'-(3-sulfopropyl)-5'-shloro-4,5-benzothiathiacyanine betaine:

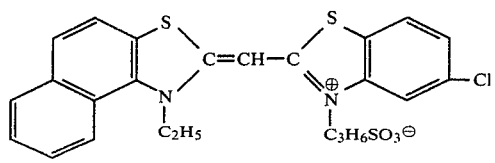

Example 6

For comparative purposes, the following 2 sensitizers were prepared following the procedures set forth in Examples 1–6; 3-ethyl-3'-(3-sulfopropyl)-4-5-4',5'-dibenzothiacyanine betaine (hereinafter designated C):

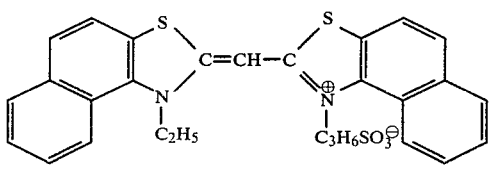

3-ethyl-3'-(3-sulfopropyl)-5'-methoxy-4,5-benzothia-thiacyanine betaine (hereinafter designated D):

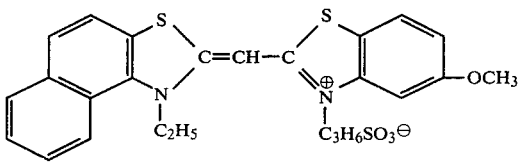

Example 7

Eight multicolor dye developer photosensitive elements were prepared according to the illustrative example in U.S. Pat. No. 3,776,726, issued Dec. 4, 1973 to Edwin H. Land, using the blue sensitizers indicated in the table, and wherein the blue-sensitive gelatino-silver iodochloro-bromide ($\frac{3}{8}$ mole % iodide) emulsion was coated at a coverage of about 120 mgs./ft.$^2$ of silver and about 80 mgs./ft.$^2$ of gelatin, and contained 2.0 mg/g of silver of 5-chloro-3'-ethyl-3-sulfobutyl-thiacyanine hydroxide and 30 mgs./ft.$^2$ of the auxiliary developer 4'-methylphenylhydroquinone. (The cyan and magenta dye developer coverages set forth in said cross-referenced example were reduced to modify contrast and color balance of the final multicolor transfer image; these changes do not affect blue sensitivity). The transparent polyester support for the image-receiving layer included an ultraviolet absorber and photoexposure was effected through this support. These multicolor elements were processed with the processing compositions set forth below and image-receiving elements used in said cross-referenced example and maintained together after transfer image formation to provide integral negative-positive reflection print. Wedge spectra transfer images were then obtained in order to determine the wave length location of the peak sensitivity of each sensitized low-iodide (ca $\frac{3}{8}$ m %) blue-sensitized emulsion and the extend of the sensitivity, i.e., the wave length where the dye ends its sensitivity. The results are shown in the following Table 1:

TABLE 1

| Sensitizer | λ max (nm) | λ extent (nm) |
|---|---|---|
| Compound 1 | 465 | 478 |
| Example 1 | 479 | 493 |
| Example 2 | 481 | 496 |
| Example 3 | 480 | 500 |
| Example 4 | 481 | 495 |
| Example 5 | 480 | 495 |
| C | 490 | 510 |
| D | 485 | 505 |

It will be observed from Table 1 that the sensitizers of the instant invention increased the peak sensitivity wave length and the extent of sensitivity relative to compound I, the most satisfactory of the prior art sensitizers. Sensitizers C and D, which are structurally similar to the sensitizers of this invention, also increased the sensitivity but in such a manner as to sensitize into the green range, i.e., greater than 500 nm. The sensitized emulsions using the blue sensitizers of Examples 1 through 5 all exhibited a sharp cut-off of sensitizer effectiveness between 490 and 500 nm.

Example 8

Multicolor photosensitive elements were prepared as in Example 7 above with the sensitizers of the instant invention and compared with a control containing compound 1. For each element, the test and controls were identical except for the spectral sensitizers. The differences in absolute numbers between elements is primarily due to negative structure changes and therefore the sensitometric data should be viewed test to control within a given element. As measured in the neutral column, the transfer image D-max, speed for the blue component, and the difference in speed of the blue components from the speed of the green component ("Bal") are set forth in the following Table 2:

TABLE 2

| Negative | Sensitizer | D-max | Speed | Bal. |
|---|---|---|---|---|
| 1 | Compound I | 2.29 | 1.47 | −10 |
|   | Example 3 | 2.28 | 1.61 | −2 |
| 2 | Compound I | 2.33 | 1.45 | −14 |
|   | Example 1 | 2.38 | 1.52 | −13 |
|   | Example 2 | 2.32 | 1.60 | −8 |
|   | Example 4 | 2.29 | 1.57 | −13 |
|   | Example 5 | 2.30 | 1.63 | −8 |
| 3 | Compound I | 2.30 | 1.63 | 0 |
|   | Example 1 | 2.33 | 1.69 | +4 |
| 4 | Compound I | 2.01 | 1.60 | +3 |
|   | Example 1 | 2.02 | 1.75 | +8 |
| 5 | Compound I | 2.03 | 1.65 | −3 |
|   | Example 1 | 2.00 | 1.72 | 0 |
|   | Example 2 | 1.99 | 1.80 | +3 |
| 6 | Compound I | 2.08 | 1.62 | −4 |
|   | Example 1 | 2.05 | 1.74 | +1 |
| 7 | Compound I | 2.01 | 1.62 | −1 |
|   | Example 1 | 2.01 | 1.73 | +6 |
|   | Example 1* | 2.02 | 1.72 | +5 |

*Second preparatory batch

Film units employing negatives 1 to 3 were processed with Processing Composition A and film units employing negatives 4 to 7 were processed with Processing Composition B.

| PROCESSING COMPOSITION A | |
|---|---|
|  | % by Weight |
| Water | 50.24 |
| Titanium dioxide | 37.3 |

-continued

| PROCESSING COMPOSITION A | |
|---|---|
|  | % by Weight |
| Carboxymethyl hydroxyethyl cellulose (Hercules Type 420 A) | 1.75 |
| Potassium hydroxide | 4.86 |
| N-phenethyl-α-picolinium bromide | 1.20 |
| 6-methyl uracil | 0.20 |
| bis-(β-aminoethyl) sulfide | 0.02 |
| Polyethylene glycol (M.W. 6000) | 0.49 |
| N-2-hydroxyethyl-N,N',N'-tris-carboxymethyl-ethylene diamine | 0.79 |
| Benzotriazole | 0.75 |
| 4-amino pyrazolopyridimidine | 0.20 |
| Colloidal silica (aqueous) | 0.49 (100% solids basis) |
|  | 1.35 |
|  | 0.30 |

| PROCESSING COMPOSITION B | |
|---|---|
|  | % by weight |
| Water | 48.1 |
| Potassium hydroxide (45%) | 12.4 |
| N-benzyl-α-picolinium bromide (50% solution in water) | 2.8 |
| Titanium dioxide | 28.6 |
| 6-methyl uracil | 0.2 |
| bis-(β-aminoethyl) sulfide | 0.03 |
| Benzotriazole | 0.91 |
| Colloidal silica aqueous dispersion (30% SiO$_2$) | 0.96 |
| N-2-hydroxyethyl-N,N',N'-tris-carboxymethyl-ethylene diamine | 0.91 |
| Carboxymethyl hydroxyethyl cellulose (Hercules Type 420 H) | 2.3 |
| Polyethylene glycol (molecular weight 6,000) | 0.6 |
| 4-amino pyrazolopyridimidine | 0.2 |
|  | 1.6 |

-continued

PROCESSING COMPOSITION B

| | % by weight |
|---|---|
| HOOC—[indole]—CH(—[indole]—NHSO$_2$C$_{16}$H$_{33-n}$)—[naphthalene-lactone C=O] | 0.3 |

Negatives 1 and 2 used a 1.05 micron silver iodobromide emulsion and the remaining negatives used a 1.5 micron silver iodobromide emulsion. All of the data in this table was determined at room temperature.

Table 2 illustrates that using the blue sensitizers of the instant invention did not result in any appreciable loss in D-max or in any adverse effect from the balance of the speed of the blue emulsion with respect to the green emulsion. The table further illustrates that faster speeds were obtained using all of the new spectral sensitizers than could be obtained with compound I. This result is particularly surprising since, as noted before, attempts to obtain faster speeds than achieved by compound I with the other thiacyanine dyes of formula I had not been successful.

In addition to conventional techniques for the direct dispersion of a particulate solid material in a polymeric, or colloidal, matrix such as ball-milling and the like, preparation of the dye developer dispersion can also be achieved by dissolving the dye in an appropriate solvent, or mixture of solvents, and the resultant solution distributed in the polymeric binder, with optional subsequent removal of the solvent(s) employed, as, e.g., by vaporization where the selected solvent(s) possesses a sufficient low boiling point or washing where the selected solvent(s) possesses a sufficiently high differential solubility in the wash medium, e.g., water, when measured against the solubility of the remaining composition components, and/or obtained by dissolving both the polymeric binder and dye in a common solvent.

For further detailed treatment of solvent distribution systems of the types referred to above, and for an extensive compilation of the conventional solvents traditionally employed in the art to effect distribution of photographic color-providing materials in polymeric binders, specifically for the formation of component layers of photographic film units, reference may be made to U.S. Pat. Nos. 2,269,158; 2,322,027; 2,304,939; 2,304,940; 2,801,171; and the like.

The polymeric acid layer comprises polymers which contain acid groups, such as carboxylic and sulfonic acid groups, which are capable of forming salts with alkali metals or with organic bases, particularly quaternary ammonium bases, or potentially acid-yielding groups, such as anhydrides or lactones, or other groups which are capable of reacting with bases to capture and retain them. The acid-reacting group is, of course, non-diffusible from the acid polymer layer. The preferred acid polymer contains free carboxyl groups and the transfer processing composition employed contains a large concentration of sodium and/or potassium ions. The acid polymers most useful are characterized by containing free carboxyl groups, being insoluble in water in the free acid form, and by forming water-soluble sodium and/or potassium salts. One may also employ polymers containing carboxylic acid anhydride groups, at least some of which preferably have been converted to free carboxyl groups prior to imbibition. While the most readily available polymeric acids are derivatives of cellulose of vinyl polymers, polymeric acids from other classes of polymers may be used. Examples of specific polymeric acids are set forth in said U.S. Pat. No. 3,362,819.

The acid polymer layer contains at least sufficient acid groups to effect a reduction in the pH of the image layer from about 13 to 14 to at least 11 or lower at the end of the imbibition period, and preferably to a pH of about 5 to 8 within a short time after imbibition. The pH of the processing composition preferably is of the order of at least 13 to 14.

It is, of course, necessary that the action of the polymeric acid be so controlled as not to interfere with either development of the negative or image transfer of unoxidized dye developers. For this reason, the pH of the image layer is kept at a level of pH 12 to 14 until the positive dye image has been formed, after which the pH is reduced very rapidly to at least about 11, preferably about pH 9 to 10, which renders unoxidized dye developer substantially nondiffusible. Unoxidized dye developers containing hydroquinonyl developing radicals diffuse from the negative to the positive as the sodium or other alkali salt. The diffusion rate of such dye image-forming components thus is at least partly a function of the alkali concentration, and it is necessary that the pH of the image layer remain on the order of 12 to 14 until transfer of the necessary quantity of dye has been accomplished. The subsequent pH reduction, in addition to its desirable effect upon image light stability, serves a highly valuable photographic function by substantially terminating further dye transfer. This processing technique thus effectively minimizes changes in color balance which might result from a longer than necessary imbibition time for multicolor transfer processes using multilayer negative.

In order to prevent premature pH reduction during transfer processing, as evidenced, e.g., by an undesired reduction in positive image density, the acid groups are so distributed in the acid polymer layer that the rate of their availability to the alkali in controllable, e.g., as a function of the rate of swelling of the polymer layer which rate in turn has a direct relationship to the diffusion rate of the alkali ions. The desired distribution can be effected by mixing the acid polymer with a polymer free of acid groups, or lower in concentration of acid groups, and compatible therewith, or by selecting an acid polymer having a relatively lower proportion of acid groups. These embodiments are illustrated in the cited patent.

The layer containing the polymeric acid can also contain a water insoluble polymer, preferably a cellulose ester, which acts to control or modulate the rate at which the alkali salt of the polymer acid is formed. Suitable are cellulose acetate, cellulose acetate butyrate, etc. The particular polymers and combinations of polymers employed in any given embodiment are, of course, selected so as to have adequate wet and dry strength and when necessary or desirable, suitable subcoats may be employed to help the various polymeric layers adhere to each other during storage and use.

The inert spacer layer, e.g., polyvinyl alcohol or gelatin, acts to "time" control the pH reduction by the polymeric acid layer. This timing is a function of the rate at which the alkali diffuses through the inert spacer layer. The pH does not drop until the alkali has passed through the spacer layer, i.e., the pH is not reduced to any significant extent by the mere diffusion into the interlayer, but the pH drops quite rapidly once the alkali diffuses through the spacer layer. Other suitable spacer layers are disclosed in U.S. Pat. No. 3,421,893.

As examples of materials for use in the image-receiving layer, mention may be made of dyeable polymers such as those disclosed and claimed in U.S. Pat. Nos. 3,148,061; 3,756,814 and 3,770,439.

As disclosed in the previously cited patents, the liquid processing composition for multicolor diffusion transfer processes comprises at least an aqueous solution of an alkaline material, e.g., sodium, hydroxide or potassium hydroxide and the like, preferably possessing a pH in excess of 12, and most preferably, a viscosity-increasing compound constituting a film-forming material of the type which, when the composition is spread and dried, forms a relatively firm and stable film. The preferred film-forming materials are high molecular weight polymers such as polymeric, water-soluble ethers which are inert to an alkaline solution such as, e.g., a hydroxyethyl cellulose, carboxymethyl hydroxyethyl cellulose or sodium carboxymethyl cellulose. Additionally, film-forming materials or thickening agents whose ability to increase viscosity is substantially unaffected if left in solution for a long period of time are capable of utilization. The film-forming material is preferably contained in the processing composition in such suitable quantities as to impart to the composition as viscosity in excess of 100 cps. at a temperature of approximately 24° C., and preferably in the order of 100,000 cps. to 200,000 cps.

For the production of the photoresponsive gelatino silver halide emulsions employed to provide the film unit, the silver halide crystals can be prepared by reacting a water-soluble silver salt, such as silver nitrate, with at least one water-soluble halide, such as ammonium, potassium or sodium bromide, preferably together with a corresponding iodide, in an aqueous solution of a peptizing agent such as a colloidal gelatin solution; digesting the dispersion at elevated temperature, to provide increased crystal growth; washing the resultant dispersion to remove undesirable reaction products and residual water-soluble salts by chilling the dispersion, noodling the set dispersion, and washing the moodles with cold water, or, alternatively, employing any of the various flocc systems, or procedures, adapted to effect removal of undesired components, e.g., the procedures described in U.S. Pat. Nos. 2,614,928; 2,614,929; 2,728,662; and the like; after ripening the dispersion at an elevated temperature in combination with the addition of gelatin and various adjuncts, for example, chemical sensitizing agents of U.S. Pat. Nos. 1,574,944; 1,623,499; 2,410,689; 2,597,915; 2,487,850; 2,518,698; 2,521,926; and the like; all according to the traditional procedures of the art, as described in Neblette, C. B. *Photography Its Materials and Processes* 6th Ed., 1962.

Optical sensitization of the emulsion's silver halide crystals, toward which the instant invention is directed, can be accomplished by contact of the emulsion composition with an effective concentration of the selected optical sensitizing dyes dissolved in an appropriate dispersing solvent such as methanol, ethanol, trifluoroethanol, pyridine, and the like; all according to the traditional procedures of the art, as described in Hamer, F. M. *The Cyanine Dyes and Related Compounds.*

Additional optional additives, such as coating aids, hardeners, viscosity-increasing agents, stabilizers, preservatives, and the like, for example, those set forth hereinafter may also be incorporated in the emulsion formulation, according to the conventional procedures known in the photographic emulsion manufacturing art.

The photoresponsive material of the photographic emulsion will preferably comprise a crystal of silver, e.g., one or more of the silver halides such as silver chloride, silver iodide, silver bromide, or mixed silver halides such as silver chlorobromide or silver iodobromide, of varying halide ratios and varying silver concentrations.

The emulsions may include the various adjuncts, or addenda, according to the techniques disclosed in the art.

As the binder for the respective emulsion strata, the aforementioned gelatin may be, in whole in in part, replaced with some other colloidal material such as albumin; casein; or zein; or resins such as a cellulose derivative (U.S. Pat. Nos. 2,322,085 and 2,327,808); polyacrylamides (U.S. Pat. No. 2,541,474); and vinyl polymers such as described in a multiplicity of readily available U.S. Patents.

In accordance with U.S. Pat. Nos. 3,415,644; 3,415,645; 3,415,646 and 3,594,165, the image-receiving elements need not be separated from superposed contact with a silver halide photosensitive element subsequent to substantial transfer image formation of the image-receiving element is transparent and a substance rendering the opaque layer is disposed between the image-receiving layer and the photosensitive-element.

Specifically, an integral diffusion transfer photographic film unit particularly adapted for the production of a dye transfer image of improved stability will be constructed, e.g., in accordance with U.S. Pat. No. 3,415,664 to include a photosensitive element comprising a laminate having in sequence as essential layers, a dimensionally stable opaque support layer, a photosensitive silver halide emulsion layer having associated therewith dye image-providing material which is soluble and diffusible in alkali at a first pH, an alkaline solution permeable polymeric acid layer containing sufficient acidifying material to effect reduction subsequent to substantial transfer dye image formation of a processing solution having the first pH to a second pH at which said dye image-providing material is insoluble and non-diffusible, and a dimensionally stable transparent support layer, the dimensionally stable support layers being the extremities of the described photographic film unit composite structure. In combination with the laminate, a rupturable container retaining an aqueous alkaline processing composition having the first pH and containing a light-reflecting agent in a quantity sufficient to mask the developed photosensitive layer and untransferred dye image-providing material, is fixedly positioned and extends transverse the leading edge of the laminate so as to effect unidirectional discharge of the container's contents between the alkaline solution permeable and dyeable polymeric layer and the photosensitive silver halide emulsion layer next adjacent thereto upon application of compressive force to the container.

The processing composition employed can contain an auxiliary or accelerating developing agent, such as p-methylamino-phenol, 2,4-diaminophenol, p-benzylaminophenol, hydroquinone, toluhydroquinone, phenylhydroquinone, 4'-methylphenylhydroquinone, etc. One can also employ a plurality of auxiliary or accelerating developing agents, such as disclosed in U.S. Pat. No. 3,039,869. Such auxiliary developing agents can be employed in the processing composition or they may be initially incorporated, at least in part, in any one or more of the silver halide emulsion strata, the strata containing the dye developers, the interlayers, the overcoat layer, the image-receiving layer, or in any other auxiliary layer, or layers, of the film unit. At least a portion of the dye developer oxidized during development may be oxidized and immobilized as a result of a reaction, e.g., an energy-transfer reaction, with the oxidation product of an oxidized auxiliary developing agent, the latter developing agent being oxidized by the development of exposed silver halide. Such a reaction of oxidized developing agent with unoxidized dye developer would regenerate the auxiliary developing agent for further reaction with the exposed silver halide.

In addition, development may be effected in the presence of an onium compound, particularly a quaternary ammonium compound; in accordance with the processes disclosed in U.S. Pat. No. 3,173,786.

It may be desirable, in certain embodiments, to expose the instant products from the emulsion side. In such instances, it is desirable to hold the photosensitive element and the image-receiving element together at one end thereof by suitable fastening means in such manner that the photosensitive element and the image-receiving element may be spread apart from their superposed processing position during exposure or, alternatively, maintained as an integral unit. A camera apparatus suitable for processing film of the type just mentioned as provided by the Polaroid Land Camera, sold by Polaroid Corporation, Cambridge, Mass., or similar camera structure such as, for example, the roll film type camera taught in U.S. Pat. No. 2,435,717 or the film pack type camera taught in U.S. Pat. No. 2,991,702. Camera apparatus of this type permit successive exposure of individual frames of the photosensitive element from the emulsion side thereof as well as individual processing of an exposed frame by bringing said exposed frame into superposed relation with a predetermined portion of the image-receiving element while drawing these portions of the film assembly between a pair of pressure members which rupture a container associated therewith and effect the spreading of the processing liquid released by rupture of the container between and in contract with the exposed photosensitive frame and the predetermined, registered area of the image-receiving element.

It will be apparent that the relative proportions of the agents of the diffusion transfer processing composition may be altered to suit the requirements of the operator. Thus, it is within the scope of this invention to modify the herein described developing compositions by the substitution of preservatives, alkalies, silver halide solvents, etc., other than those specifically mentioned, in accordance with practices well known in the art. When desirable, it is also contemplated to include in the developing composition, components such as restrainers, accelerators, etc. Similarly, the concentration of various components may be varied over a wide range, and when desirable, adaptable components may be disposed in the photosensitive element, prior to exposure, in a separate permeable layer of the photosensitive element and/or in the photosensitive emulsion.

The support layers referred to may comprise any of the various types of conventional rigid or flexible supports, e.g., glass, paper, metal, and polymeric films of both synthetic and those derived from naturally occurring products. Suitable materials include paper, aluminum, polymethacrylic acid methyl and ethyl esters, vinyl chloride polymers, polyvinyl acetal, polyamindes such as nylon, polyesters such as polymeric films derived from ethylene glycol terephthalic acid, and cellulose derivatives such as cellulose acetate, triacetate, nitrate, propionate, butyrate, acetate-propionate, or acetate-butyrate.

The nature and construction of rupturable containers is well understood in the art; see, for example, U.S. Pat. Nos. 2,543,181 and 2,634,886.

By appropriate selection of the image-receiving element materials from among suitable known opaque and transparent materials, it is possible to obtain either a colored positive relection print or a colored positive transparency.

While a rupturable container provides a convenient means for spreading a liquid processing composition between layers of a film unit to permit the processing to be carried out within a camera apparatus, the practices of this invention may be otherwise effected. For example, a photosensitive element, after exposure in suitable apparatus and while preventing further exposure thereafter to actinic light, may be removed from such apparatus and permeated with the liquid processing composition, as by coating the composition on said photosensitive element or otherwise setting said element with the composition, following which the permeated, exposed photosensitive element, still without additional exposure to actinic light, is brought into contact with the image-receiving element for image formation in the manner heretofore described.

In addition to the described layers, it will be recognized that the film unit may also contain one or more subcoates or interlayers, which, in turn, may contain one or more additives such as plasticizers, for the purpose, for example, of improving adhesion.

Various changes and modifications can be made in the products of this invention without departing from the spirit and scope thereof. The various embodiments set forth herein are intended for illustration purposes only and are not intended to limit the invention.

What is claimed is:

1. A photosensitive element comprising a support carrying:
    (a) a red-sensitive silver halide emulsion having associated therewith a cyan dye developer;
    (b) a green-sensitive halide emulsion having associated therewith a magenta dye developer; and
    (c) a blue-sensitive silver halide emulsion having associated therewith a yellow dye developer; said blue-sensitive silver halide emulsion additionally including a 3,3'-disubstituted, 4,5-benzothia-thiacyanine betaine of the formula:

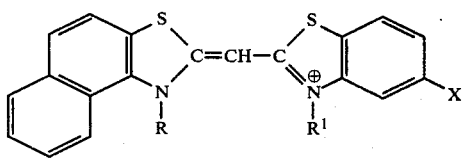

wherein R is ethyl or sulfopropyl, R¹ is sulfopropyl when R is ethyl and R¹ is ethyl when R is sulfopropyl and X is hydrogen.

2. The element of claim 1 wherein the blue-sensitive emulsion contains less than about 2 mole percent iodide.

3. The element of claim 2 wherein said blue-sensitive emulsion contains about ⅝ mole percent iodide.

4. A photographic film unit which comprises, in combination:
   a photosensitive element having a diffusion transfer image-receiving element affixed at least one edge thereof, said photosensitive element comprising a support carrying:
   (a) a red-sensitive silver halide emulsion having associated therewith a cyan dye developer;
   (b) a green-sensitive silver halide emulsion having associated therewith a magenta dye developer;
   (c) a blue-sensitive silver halide emulsion having associated therewith a yellow dye developer; said blue-sensitive silver halide emulsion additionally including a 3,3'-disubstituted, 4,5-benzothia-thiacyanine betaine of the formula:

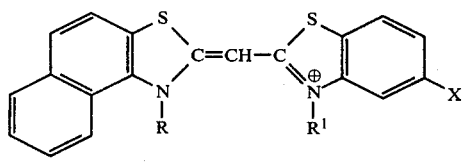

wherein R is ethyl or sulfopropyl, R¹ is sulfopropyl when R is ethyl and R¹ is ethyl when R is sulfopropyl and X is hydrogen;
   said diffusion transfer image-receiving element comprising a support layer carrying:
   an alkaline processing composition permeable and dyeable layer wherein said photosensitive and said image-receiving elements are adapted to be superposed, the support layers of each comprising the extremities of the superposed structure.

5. The film unit of claim 4 including a rupturable container retaining an aqueous alkaline processing composition affixed to one edge of said photosensitive and said image-receiving elements and adapted to rupture to distribute its contents intermediate said superposed photosensitive and image-receiving elements.

6. The film unit of claim 5 wherein said image-receiving element support layer is transparent.

7. The film unit of claim 6 in which said unit is a composite structure comprising said photosensitive element and said image-receiving element permanently affixed to the other in superposed relationship, the support layers of each of said elements being outermost.

8. The film unit of claim 4 wherein said blue-sensitive emulsion contains less than 2 mole percent iodide.

9. The film unit of claim 8 wherein said blue-sensitive emulsion contains about 5/8 mole percent iodide.

10. The film unit of claim 4 wherein (c) consists essentially of said emulsion, said dye developer and said betaine.

11. A photosensitive element comprising a support carrying a light-sensitive silver halide emulsion optically sensitized with a 3,3'-disubstituted 4,5-benzothiacyanine of the formula:

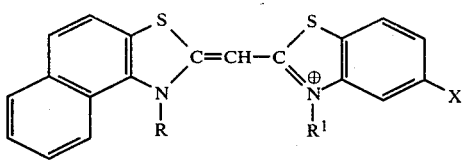

wherein R is ethyl or sulfopropyl, R¹ is sulfopropyl when R is ethyl and R¹ is ethyl when R is sulfopropyl and X is hydrogen.

12. The element of claim 11 wherein said emulsion contains less than about 2 mole percent iodide.

13. The element of claim 12 wherein said emulsion contains about ⅝ mole percent iodide.

14. The element of claim 11 which includes a layer containing a yellow dye developer.

15. A 3,3'-disubstituted, 4,5-benzothia-thiacyanine betaine of the formula:

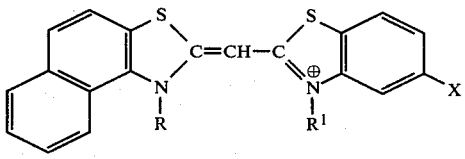

wherein R is ethyl, or sulfopropyl, R¹ is sulfopropyl when R is ethyl and R¹ when R is sulfopropyl, and X is hydrogen.

* * * * *